(12) United States Patent
Slama

(10) Patent No.: US 8,004,671 B2
(45) Date of Patent: Aug. 23, 2011

(54) METHOD FOR IDENTIFYING A TRANSPARENT OBJECT WITH THE AID OF ITS ABSORPTION SPECTRUM

(75) Inventor: Michael Slama, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 316 days.

(21) Appl. No.: 12/215,396

(22) Filed: Jun. 27, 2008

(65) Prior Publication Data

US 2009/0002709 A1    Jan. 1, 2009

(30) Foreign Application Priority Data

Jun. 29, 2007  (DE) .......................... 10 2007 030 384

(51) Int. Cl.
*C12M 1/20* (2006.01)
*G01N 21/27* (2006.01)

(52) U.S. Cl. ........ 356/246; 356/432; 356/425; 356/234; 435/288.4; 422/915; 422/941

(58) Field of Classification Search ............... 356/433, 356/244–246
See application file for complete search history.

(56) References Cited

U.S. PATENT DOCUMENTS

| | | | |
|---|---|---|---|
| 5,046,841 A | | 9/1991 | Juds et al. |
| 5,132,096 A | * | 7/1992 | Hoots et al. .............. 422/82.09 |
| 5,216,487 A | * | 6/1993 | De Bruin et al. .......... 356/432 |
| 5,670,118 A | * | 9/1997 | Sponholtz ................. 422/102 |
| 5,686,210 A | * | 11/1997 | Sharman ..................... 430/30 |
| 5,719,939 A | | 2/1998 | Tel |
| 5,757,001 A | | 5/1998 | Burns |
| 6,555,190 B1 | * | 4/2003 | Tsai ........................ 428/36.6 |
| 6,595,427 B1 | | 7/2003 | Soni |
| 7,438,854 B2 | * | 10/2008 | Oshima ................... 422/82.05 |
| 2004/0222136 A1 | | 11/2004 | Popp et al. |
| 2005/0018013 A1 | | 1/2005 | Nelson |
| 2005/0243305 A1 | | 11/2005 | Vig |
| 2007/0035719 A1 | * | 2/2007 | Hiltner et al. ................ 356/71 |
| 2007/0035819 A1 | | 2/2007 | Bahatt |

FOREIGN PATENT DOCUMENTS

| | | |
|---|---|---|
| DE | 2924605 A1 | 4/1980 |
| DE | 32 16 867 C2 | 12/1982 |
| DE | 40 00 197 A1 | 7/1990 |
| DE | 101 24 917 A1 | 12/2002 |
| DE | 10155780 A1 | 5/2003 |
| EP | 0233316 A2 | 8/1987 |
| EP | 0 772 843 B1 | 5/1997 |
| GB | 2 09 7 979 A | 11/1982 |
| WO | WO 2006/055293 A1 | 5/2006 |

OTHER PUBLICATIONS

Jugulum et al.; "Comparison Between Mahalanobis-Taguchi System and Artificial Neural Networks", Quality Engineering, vol. 10, No. 1, pp. 60-73, (2002).

European Search Report dated Jul. 8, 2010, for EP Application No. 08 00 9998.

* cited by examiner

*Primary Examiner* — Gregory J Toatley
*Assistant Examiner* — Rebecca C Slomski
(74) *Attorney, Agent, or Firm* — Finnegan, Henderson, Farabow, Garrett & Dunner, L.L.P.

(57) ABSTRACT

The present invention relates to a method for identifying transparent objects, for example measurement cuvettes, with the aid of their absorption spectrum and therefore makes it possible to protect articles against forgery or imitation.

22 Claims, 2 Drawing Sheets

METHOD FOR IDENTIFYING A TRANSPARENT OBJECT WITH THE AID OF ITS ABSORPTION SPECTRUM

The present invention relates to a method for identifying transparent objects and therefore makes it possible to protect articles against forgery or imitation.

Establishing the authenticity of a product is of great economic importance in view of increasing product piracy. Furthermore, especially in the case of technical products or articles which are used as components within a technical system, it is necessary to ensure that the product has particular qualitative properties in order to guarantee error-free functioning of a method or a device. In many technical fields, it is furthermore necessary to ensure particular quality standards, so that the manufacturers of the relevant articles or systems are required to instigate measures which allow authenticity testing of articles, spare parts and the like.

Examples of transparent articles, the authenticity of which is crucial for the quality of the method in which they are used, are for example measurement cells such as cuvettes, cuvette rotors or microtitration plates, which are used in an optical detection method. Test methods for determining clinically relevant parameters, for example to diagnose coagulation parameters, are often evaluated with the aid of photometric detection systems. Clinical laboratories mainly employ fully automatic analysis equipment which allows not only automatic conduct of the test methods, but also the determination of standardized test results. In order to ensure that the automated methods deliver reliable test results, it is necessary for all individual test-relevant components to fulfill specific requirements stipulated by the manufacturer or to be in the state which is categorically necessary for their use. This also pertains inter alia to the reaction vessels or measurement cells being used, for example cuvettes, cuvette rotors or microtitration plates which contain the samples to be analyzed, the optical property of which is intended to be determined. The reaction vessels recommended by the manufacturer generally not only have specific design properties such as shape, size, layer thickness etc., but also usually consist of a material which exhibits no absorption or only little absorption in the spectral range being used. Using inauthentic copies of reaction vessels, of which the user may possibly not even be aware, entails the risk that large discrepancies or errors may occur when measuring the turbidity or the scattered light owing to differences in the material composition. A further risk is presented by reaction vessels which may undergo interactions with the analytes to be determined, the sample or the reaction mixture, owing to their material properties. This problem may be made particularly clear with reference to the example of coagulation diagnostic methods: if the surface of the reaction vessel or the measurement cell, which comes in contact with the reaction mixture, is constituted so that uncontrolled activation of the coagulation takes place, then reliable determination of the coagulation reaction cannot be carried out. Erroneous measurement results and uncontrolled reaction conditions can lead to incorrect diagnoses, which in the worst case may have serious health consequences for the patient in question.

Various characterization methods and corresponding optical identification methods which make it possible to mark objects or documents and detect forgeries are known in the prior art, which therefore allow the articles to be protected against imitation.

Patent Specification DE 101 55 780 A1 describes a method in which a three-dimensional irreproducible random pattern is generated during production of the article to be protected, for example particles of opaque material which are scattered into a transparent plastic. The physical pattern is then scanned with the aid of a sensor and stored as a characterizing feature. Patent Specification U.S. Pat. No. 5,719,939 describes in particular the use of loosely assembled nonwoven fibers (fleeces) in a transparent material.

Patent Specification EP 0 772 843 B1 describes a method in which a three-dimensional marking is produced on the surface of the object by roughening during production of the article to be protected. The pattern is then analyzed and stored with the aid of imaging or image-processing systems. A similar method is described in Patent Specification DE 32 16 867 C2. Here, the article is likewise identified with the aid of topographic surface features, heights and spacings of the irregularities being digitally measured and analyzed.

Patent Application DE 40 00 197 A1 has described tokens and devices for their validation. The features characterizing the tokens are light-diffracting indentations in the surface of the tokens, for example prismatic facets, reflective facets or diffraction gratings. The tokens are tested for their validity with the aid of an optical sensor, which measures the position and the intensity of a diffracted light beam.

A serious disadvantage of the described methods for characterizing and identifying articles is that the optical properties of the article are significantly modified by the markings, for example by scattering in opaque particles or by processing the surface. Such methods are not therefore suitable for the characterization of articles whose optical properties are subject to specific requirements, and in particular not-for the characterization of transparent articles which are a component of an optical test method.

It was therefore an object of the invention to provide a method which makes it possible to identify transparent objects having specific optical properties, or to identify forgeries. The characterization of the transparent objects should above all be distinguished in that firstly it does not compromise the actual intended purpose of the object, secondly it can be produced without great technical outlay and inexpensively, and thirdly it is difficult to imitate.

The term "identification" in the context of the present invention is intended to mean determining the identity of an object in relation to a feature of a reference object.

The object is achieved by providing the methods and articles according to the invention as described in the claims.

The present invention relates to a method for identifying a transparent object with the aid of its absorption spectrum, or for testing the authenticity of a transparent object. Transparent objects such as cuvettes, cuvette rotors, microtitration plates or capillaries, which are used in a photometric detection system, usually consist of a material which exhibits no absorption or only little absorption in the spectral range being used. According to the present invention, the object to be identified consists of a material which contains at least one, and preferably at least two light-absorbing substances (colorants).

The material of which the transparent article to be identified consists may be glass or a plastic. The method according to the invention is suitable in particular for identifying transparent objects which consist of quartz glass, in particular quartz glass which has been fused from natural crystal (rock crystal), synthetic quartz glass which has no OH absorption (for example SUPRASIL® 300, Heraeus Quartzglas GmbH, Hanau, Germany) or which consist of crown glass with a high proportion of potassium oxide or borosilicate glass (for example Borofloat®, Schott AG, Mainz, Germany). The method according to the invention is furthermore suitable for the identification of transparent objects which consist of plastic, in particular a plastic from the group polypropylene, polystyrene, polyethylene, polyvinyl chloride, polymethyl methacrylate and polyethylene terephthalate.

The colorants may be soluble dyes and/or insoluble pigments, which may be added to the glass or the plastic before or during processing so that a homogeneously colored material is obtained. If the transparent article to be identified is a measurement cell which is intended to be used in an optical test method, then when using colorants it is necessary to ensure that the measurement cell subsequently has a sufficient transmittance so that it can be used properly in the optical measurement method.

A multitude of dyes known to the person skilled in the art may be used for coloring transparent articles to be identified or for coloring the transparent material. The most important class of the synthetic dyes are azo dyes. Azo dyes have the general formula R—N=N—R', where N stands for nitrogen, R and R' respectively stand for an organic radical, preferably an aromatic hydrocarbon. Azo dyes are distinguished by high color and light fastness. They are often available as dye concentrates in polymeric carriers, so-called master batches, and may be added to the plastic compound in the desired concentration before the manufacture of plastic parts, for example cuvettes.

As is known, the absorption spectrum of a mixture of a plurality of light-absorbing components ("colorants") is formed additively from the absorption spectra of the individual components. The resulting characteristic absorption spectrum of the mixture differs from the absorption spectra of the individual components. The inventive characterization of a transparent object, or the protection against forgery or imitation, thus consists in using a material which has a characteristic absorption spectrum owing to the use of at least one, preferably at least two light-absorbing substances, in order to produce the transparent object. The concentration of the colorant is preferably selected to be so low that it does not overly restrict the dynamic measurement range of the optical detection system but is high enough so that absorption can still reliably be measured. The particular advantage of this characterization is that it can be imitated with only relatively high efforts. The work which would need to be done without knowing the type and concentration of the colorant being used, in order to produce a material with an identical absorption spectrum, would make imitation practically unviable.

The present invention therefore relates to a measurement cell, for example in the form of a cuvette, a cuvette rotor, a microtitration-plate or a capillary, which is suitable for use-in a photometric detection system. A measurement cell according to the invention consists of a transparent material, preferably glass or plastic, which contains at least one, preferably at least two light-absorbing substances (colorants) and therefore has a characteristic absorption spectrum. The at least one light-absorbing substance is preferably an azo dye.

The method according to the invention for identifying a transparent object is furthermore characterized in that the absorption of the transparent object is measured at least at two different wavelengths and the absorption measurement values are compared with previously ascertained absorption measurement values characteristic of the object to be identified, which have been stored as reference values. The comparison of the absorption measurement values of the object to be identified with the reference values, i.e. the testing for authenticity of the object, is preferably carried out by using so-called pattern recognition techniques.

Pattern recognition techniques are multivariate evaluation methods which make it possible to simultaneously evaluate at least two variables, here absorption measurement values.

Examples of pattern recognition techniques which are suitable for use in the method according to the invention are principal component analysis (PCA), soft independent modeling of class analogy (SIMCA), artificial neural network (ANN), discriminant analysis and variants of said techniques (see for example Martens, H. & T Naes: Multivariate calibration. John Wiley & Sons Ltd, 1989, ISBN 0 471 90979 3; Otto, M.: Chemometrie [chemometry], VCH, 1997, ISBN 3 527 28849 X; Zell, A.: Simulation Neuronaler Netze [simulation of neural networks], Addison Wesley, 1994, ISBN 3 89319 554 8).

If the absorption values measured for an object are now entered in a coordinate system whose dimensionality corresponds to the number of wavelengths used, then the object will lie at a defined position in higher-dimensional space according to the absorption behavior. An object which exhibits no absorption or only very little absorption would have its position near the origin of the coordinate system in this space (see FIG. 1(1)). A decision about whether an object to be identified is identical or different to a reference object may be made in the simplest case by using the Euclidean distance or the Mahalanobis distance between the reference object and the object to be identified (see also Jugulum, R. and Monplaisir, L. [2002] Comparison between Mahalanobis-Taguchi System and Artificial Neural Networks. Quality Engineering 10, 60-73).

The position of the object to be identified is preferably compared not only with the position of a single reference object, but with a reference class. A reference class consists of a collection of a plurality of measurements obtained after single calibration using a plurality of instruments and a plurality of batches of the relevant transparent object, in order to reflect the variance. The comparison is carried out using the vector, which points from the centroid of the reference class to the object to be identified. The absolute value of the vector is subsequently set in relation to the distribution of the reference class and evaluated by methods of statistics, for example by determining the distance from the midpoint of the reference class while taking the variance into account. An assessment of whether the object to be identified differs significantly from the reference class is obtained as a result.

If the direction of the difference vector is also taken into account besides the absolute value of the difference vector and the distribution of the reference class, then additional information may be found when there is a discrepancy of the object to be identified. Differing objects may be objects which contain a false light-absorbing component, or a false concentration of a light-absorbing component, as well as objects which for example have material defects, such as a discrepant wall thickness or scratches that scatter the incident light.

A particular embodiment of the method according to the invention consists in combining a group of a plurality of identical transparent objects to be identified in order to form a class with its own distribution. The term "identical transparent objects" is intended to mean a group of objects of the same type, which should have the same absorption properties. If for example the last 10 samples of a long measurement series are respectively combined to form a class, a so-called test class, and the distance from the reference class is compared while taking the distribution into account, then a decision criterion is obtained which is relatively unaffected by random variations (see FIG. 1 (4) and (5)).

The invention therefore also relates to a method for testing the authenticity of a plurality of identical transparent objects, which contain at least one light-absorbing substance. To this end the absorption of a plurality of transparent reference objects is determined respectively at least at two different wavelengths. The absorption measurement values are stored as reference values, and a reference class is formed from the reference values. The absorption of each of the objects to be tested for authenticity is determined at the at least two different wavelengths. The absorption measurement values are stored, and a test class is formed from the absorption measurement values of the objects. The values of the test class are subsequently compared with the values of the reference class. The comparison of the values of the test class with the values of the reference class is preferably carried out with the aid of a multivariate evaluation method. The comparison of the values of the test class with the values of the reference class may be carried out using a distance measure, for example from the group Euclidean distance or Mahalanobis distance.

The method according to the invention is preferably carried out automatically. In the case of transparent reaction vessels, which are intended for use in an optical analysis instrument, the authenticity of the reaction vessels is preferably tested before sample liquid or test reagents are aliquoted into the reaction vessels. The absorption of the reaction vessels is preferably measured in a photometer, with a light source emitting a light beam through the reaction vessels to be tested and a detector measuring the intensity of the transmitted light and converting it into an electrical signal. It is particularly preferable to use a photometer which provides any desired wavelength between $\lambda=220$ and 1000 nm, preferably between $\lambda=380$ and 900 nm, so that the required absorption measurements at different wavelengths can be carried out in rapid succession one after the other. The light sources may be polychromatic light sources, in which case the light will need to be spectrally dispersed with the aid of a diffraction grating, or a combination of a plurality of monochromatic light sources may be used, for example lasers or light-emitting diodes (LEDs).

If it is found in the authenticity test according to the invention that the absorption measurement values of the object to be tested lie within a preestablished acceptance range of the absorption measurement values of the reference class, then the object is approved for further intended use. If however it is found that the absorption measurement values of an object to be tested lie outside a preestablished acceptance range of the absorption measurement values of the reference class, then the object is not approved for further intended use.

The invention also relates to a device which is capable of automatically carrying out the method according to the invention for testing the authenticity of a transparent object. Such a device is distinguished in that it comprises a) means for measuring the absorption of a transparent object at least at two wavelengths (for example a photometer), b) means for storing the absorption measurement values or data (for example a semiconductor memory, an optical or magnetic storage medium, for example a hard disk) and c) means for controlling the conduct of the comparison of the absorption measurement values of the transparent object to be tested for authenticity with the values of the reference class (for example software, computer program, algorithm), or means for controlling the conduct of the comparison of the values of a test class of a plurality of identical transparent objects with the values of a reference class.

In a preferred embodiment, the means c) are means for carrying out a multivariate evaluation method (for example software, computer program, algorithm).

The apparatus preferably also has means for outputting measurement results (for example an electronic display instrument, a monitor, a data plotter, a printer and/or remote data link).

The following exemplary embodiments serve to illustrate the present invention and are not to be regarded as a restriction.

EXAMPLE 1

Thin colored transparent films of single-colored polypropylene (Leitz brochure sleeves; 150 µm thick transparent PVC hard films) were adhesively bonded onto colorless transparent plastic cuvettes (Uvette®, Eppendorf, Hamburg, Germany):

Type 1: without color film
Type 2: yellow color film
Type 3: red color film
Type 4: yellow and red color films on top of one another.

Figure 1:
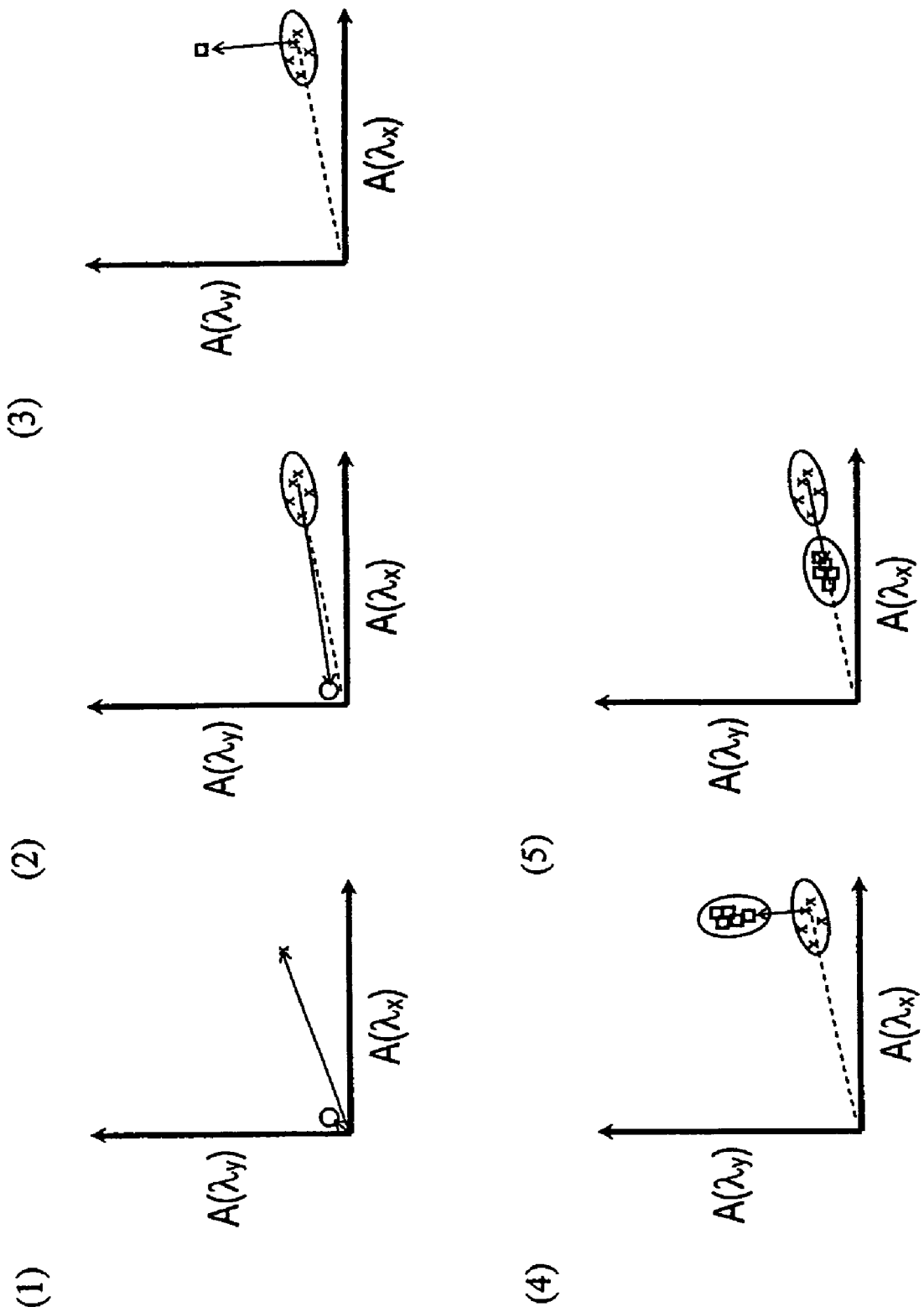
FIG. 1 illustrates the principle of the pattern recognition with two variables. $A(\lambda_x)$ corresponds to the absorption of an object to be identified at a wavelength $\lambda_x$. $A(\lambda_y)$ corresponds to the absorption of an object to be identified at a wavelength $\lambda_y$. (1) Origin vector to reference ($\times$) and random sample (circle). A colorless standard cuvette was used as a random sample. (2) The vector from the centroid of the reference class to the random sample has the length of the origin vector -and points in the direction of the origin. (3) The vector from the reference class to the random sample (square) when using other light-absorbing components ("colorant"). (4) Comparison of reference class and random sample class. Other colorants in the random sample class. (5) Comparison of reference class and random sample class. Thinner wall thickness of the cuvettes of the random sample class or different concentration of the colorants.
Figure 2:
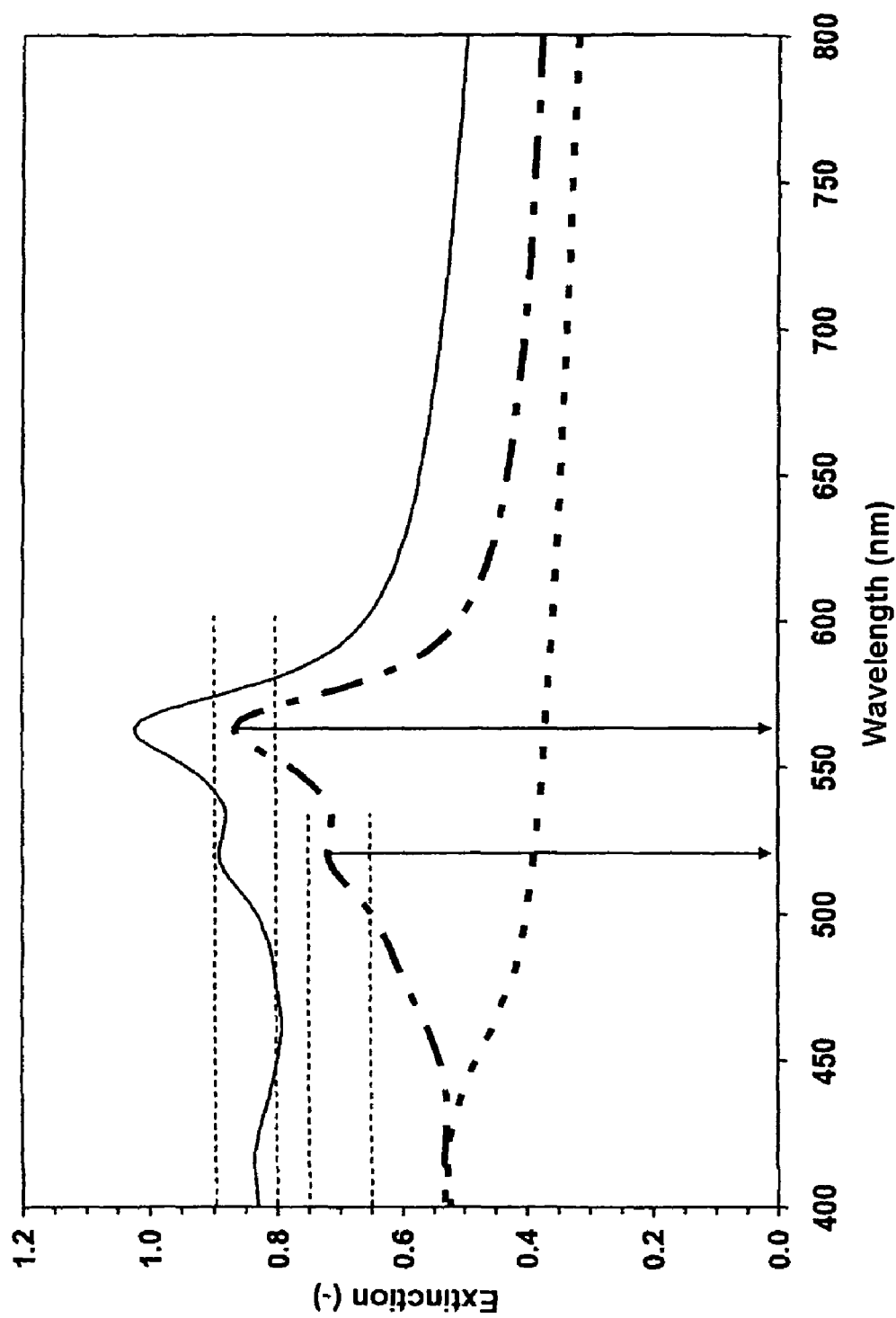
FIG. 2 shows the absorption spectra of three different-colored plastic cuvettes (see Example 1). Yellow color film (type 2): dotted line; red color film (type 3): dashed line; yellow and red color films together (type 4): solid line.

A spectrum in the visible range was then recorded in a spectrometer (Perkin Elmer) (see FIG. 2).

The way in which the cuvette was tested before use will be described by way of example for type 3 cuvettes. The following algorithm was used for this:

1. Absorption measurement at 566 nm (see right-hand arrow),
2. Absorption measurement at 516 nm (see left-hand arrow),
3. Acceptance of the cuvette only if:
   $A_{566\ nm} > 0.80$ (see auxiliary line in FIG. 2) and
   $A_{566\ nm} < 0.90$ (see auxiliary line in FIG. 2) and
   $A_{516\ nm} > 0.65$ (see auxiliary line in FIG. 2) and
   $A_{516\ nm} < 0.75$ (see auxiliary line in FIG. 2).

Otherwise, the cuvette was rejected.

In order to determine a coagulation reaction in a type 3 cuvette, the cuvette was initially heated to 37° C. and 75 µL of normal plasma and 150 µL of isotonic saline were pipetted into the cuvette. Next, 450 µL of a prothrombin time reagent (Innovin®, Dade Behring Marburg GmbH, Marburg, Germany) were added and the reaction was determined continuously at 405 nm. A coagulation reaction may be measured without problems even in a colored cuvette.

The invention claimed is:

1. A method for testing the authenticity of at least one transparent measurement cell consisting of a transparent material, the transparent material comprising at least one colorant in the material, the method comprising:

providing measurement values of an absorption of a plurality of transparent reference measurement cells at a plurality of wavelengths, storing absorption measurement values as reference values, and forming a reference class;

using a photometric detection device to measure an absorption of the at least one transparent measurement cell to be tested for authenticity at the plurality of wavelengths; and comparing the absorption measurement values of the at least one transparent measurement cell to be tested for authenticity with the values of the reference class.

2. A method for testing the authenticity of a plurality of transparent measurement cells comprising a group of measurement cells of the same type, the group of measurement cells consisting of a transparent material comprising at least one colorant in the material, the method comprising:

providing measurement values of an absorption of a plurality of transparent reference measurement cells at a plurality of wavelengths, storing absorption measurement values as reference values, and forming a reference class;

using a photometric detection device to measure an absorption of the plurality of transparent measurement cells to be tested for authenticity at the plurality of wavelengths, storing absorption measurement values, and forming a test class; and comparing values of the test class with the values of the reference class.

3. The method as claimed in claim 1, wherein the at least one transparent measurement cell to be tested for authenticity comprises at least two colorants in the material.

4. The method as claimed in claim 1, wherein the at least one transparent measurement cell to be tested for authenticity comprises at least one colorant from the azo dye group in the material.

5. The method as claimed in claim 1, wherein measuring an absorption of the at least one transparent measurement cell to be tested for authenticity at the plurality of wavelengths includes measuring at wavelengths in a range from 220 nm to 1000 nm.

6. The method as claimed in claim 1, wherein the number of transparent reference measurement cells is greater than the number of wavelengths used.

7. The method as claimed in claim 1, wherein comparing the absorption measurement values of the at least one transparent measurement cell to be tested for authenticity with the values of the reference class includes using a distance measure.

8. The method as claimed in claim 1, wherein comparing the absorption measurement values of the at least one transparent measurement cell to be tested for authenticity with the values of the reference class includes comparing the absorption measurement values of the at least one transparent measurement cell to be tested for authenticity with the centroid of the values of the reference class by using a distance measure.

9. The method as claimed in claim 2, wherein comparing values of the test class with the values of the reference class includes using a distance measure.

10. The method as claimed in claim 2, wherein comparing values of the test class with the values of the reference class includes comparing values of the test class with the centroid of the values of the reference class by using a distance measure.

11. The method as claimed in claim 7, wherein the distance measure includes one of Euclidean distance and Mahalanobis distance.

12. The method as claimed in claim 1, wherein comparing the absorption measurement values of the at least one transparent measurement cell to be tested for authenticity with the values of the reference class includes use of a multivariate evaluation method.

13. The method as claimed in claim 2, wherein comparing values of the test class with the values of the reference class includes use of a multivariate evaluation method.

14. The method as claimed in claim 12, wherein the multivariate evaluation method is selected from one of principal component analysis, soft independent modeling of class analogy, artificial neural network, and Mahalanobis-Taguchi system.

15. The method as claimed in claim 1, wherein the at least one transparent measurement cell comprises a transparent material and the transparent material is glass or plastic.

16. The method as claimed in claim 15, wherein the glass is natural quartz glass, synthetic quartz glass, or borosilicate glass.

17. The method as claimed in claim 15, wherein the plastic is polypropylene, polystyrene, polyethylene, polyvinyl chloride, polymethyl methacrylate, or polyethylene terephthalate.

18. The method as claimed in claim 1, wherein the at least one transparent measurement cell is a cuvette.

19. The method as claimed in claim 1, wherein the at least one transparent measurement cell is a cuvette rotor.

20. The method as claimed in claim 1, wherein the at least one transparent measurement cell is a microtitration plate.

21. A device for automatically carrying out a method for testing the authenticity of the at least one transparent measurement cell according to claim 1, comprising:

means for measuring the absorption of the at least one transparent measurement cell at the plurality of wavelengths, means for storing the absorption measurement values, and means for controlling conduct of the comparison of the absorption measurement values of the at least one transparent measurement cell to be tested for authenticity with the values of the reference class, wherein the device is associated with the transparent measurement cell comprising at least one colorant in the material.

22. The device as claimed in claim 21, wherein the means for controlling the conduct of the comparison of the absorption measurement values of the at least one transparent measurement cell to be tested for authenticity with the values of the reference class comprises installed software.

* * * * *